United States Patent [19]

Moriya et al.

[11] Patent Number: 5,801,827
[45] Date of Patent: Sep. 1, 1998

[54] ANALYSIS DEVICE USING CHEMICAL COMBUSTION FLAME

[75] Inventors: Kazuo Moriya; Yasushi Terui, both of Hitachinaka; Hayato Tobe, Mito; Yoshisada Ebata; Hisashi Kimoto, both of Hitachinaka, all of Japan

[73] Assignee: Hitachi, Ltd., Tokyo, Japan

[21] Appl. No.: 851,291

[22] Filed: May 5, 1997

[30] Foreign Application Priority Data

May 7, 1996 [JP] Japan .................................. 8-112525

[51] Int. Cl.$^6$ .................................................. G01N 21/72
[52] U.S. Cl. .................................... 356/315; 356/417
[58] Field of Search ............................. 356/315, 417

[56] References Cited

FOREIGN PATENT DOCUMENTS 2-59423 B2  12/1990  Japan .

*Primary Examiner*—F. L. Evans
*Attorney, Agent, or Firm*—Kenyon & Kenyon

[57] ABSTRACT

In an analysis device, an auxiliary gas supplied from a compressor 1 is introduced from an auxiliary gas inlet 3 via a pipe 2 to a burner through a pressure regulator 5, a pressure meter 6, a pressure switch 7 and a connecting joint 8. On the other hand, a combustible gas supplied from a gas bomb 9 is introduced from a combustible gas inlet 11 via a pipe 10 to the burner through a first electromagnetic valve 12, a pressure regulator 13, a pressure meter 14, a needle valve 15, a second electromagnetic valve 16 and a connecting joint 17 and further via a tube. An auxiliary gas use block 4, on which auxiliary gas flow controlling elements such as the pressure regulator 5, the pressure meter 6 and the pressure switch 7 are secured, is provided independent and separated from a combustible gas use block 18, on which combustible gas flow controlling elements such as the first electromagnetic valve 12, the pressure regulator 13, the pressure meter 14, the needle valve 15 and the second electromagnetic valve 16 are secured. Whereby the analysis device using chemical combustion flame having an element safety is provided in which possible danger caused by such as the gas leakage and the gas mixing between the combustible gas passage and the auxiliary gas passage is further reduced.

11 Claims, 3 Drawing Sheets

ANALYSIS DEVICE USING CHEMICAL COMBUSTION FLAME

BACKGROUND OF THE INVENTION

1. Field of the Invention

The present invention relates to an analysis device using chemical combustion flame and, in particular, relates to an analysis device using chemical combustion flame such as a flame photometer and an atomic absorption photometer wherein chemical combustion flame is formed by making use of combustible gas and auxiliary gas, and then a sample is introduced into the chemical combustion flame to measure photo emission and/or photo absorption of the sample.

2. Description of Conventional Art

In an analysis device using chemical combustion flame such as a flame photometer and an atomic absorption photometer which is primarily used for quantitative analysis of metal elements, because of safety reasons such as for preventing leakage of combustible gas and auxiliary gas used for forming chemical combustion flame, gas passages are formed within a plate made of a metal or plastic material and several elements for controlling gas flow in the gas passages are provided on the plate as disclosed, for example, in JP-B-2-59423(1990).

Such conventional art is more specifically explained with reference to FIGS. 3, 4 and 5, wherein FIG. 3 shows a schematic diagram of the conventional analysis device using chemical combustion flame, FIG. 4 shows a gas flow passage diagram thereof and FIG. 5 shows a cross sectional view of a plate constituting a gas flow control unit therefor.

For the first time, FIG. 3 is explained. Air serving as the auxiliary gas supplied from a compressor 1 is introduced from an auxiliary gas inlet 3 via a pipe 2 to a burner 24 through a pressure regulator 5, a pressure meter 6, a pressure switch 7 and a connecting joint 8 arranged on a plate 21 and via a tube 22. On the other hand, such as acetylene gas and propane gas serving as the combustible gas supplied from a gas bomb 9 is introduced from a combustible gas inlet 11 via a pipe 10 to the burner 24 through an electromagnetic valve 12, a pressure regulator 13, a pressure meter 14, a needle valve 15, another electromagnetic valve 16 and a connecting joint 17 arranged on the plate 21 and further via a tube 23. The air and the combustible gas introduced into the burner 24 are mixed inside the burner 24 and are flown out from the upper portion thereof and fired to form chemical combustion flame 25. Further, a sample 27 contained in a test tube 26 is introduced into the burner 24 and is atomic-vaporized, and then the photo emission and photo absorption caused by the atomically vaporized sample is measured.

The above explained elements, namely gas flow controlling elements constituting the gas flow controlling unit are respectively secured on the major plane of the plate 21 by respective screws 19 as seen from FIG. 3. The channels formed inside the plate 21 form the gas flow passages to which the respective gas flow controlling elements are connected as illustrated FIG. 4. Further, as illustrated in FIG. 5 many holes led to one of the respective channels are formed from the upper and bottom faces and side faces of the plate 21 to connect the channels via the respective gas flow controlling elements to constitute the respective gas flow passages.

The plate 21 and the respective gas flow controlling elements placed on the plate 21 are generally sealed at their contacting surfaces by O rings so as to prevent gas leakage from the respective holes led to the associating channels and are firmly secured each other via the screw 19 and the corresponding threaded holes 29 formed on the plate 21. The locations of the channels within the plate 21 and the threaded holes 29 formed on the plate 21 and used for securing the respective gas controlling elements are designed so as not to interfere each other. Further, the leading holes formed from the bottom face and the side faces of the plate 21 are plugged by pressing balls 30 coated with adhesive.

The above explained conventional device in which the gas flow controlling elements are arranged on the plate having the gas flow channel passages therein is advantageous with regard to its excellent safety, its limited installation area and so on in comparison with a devices in which the gas flow controlling elements are connected via respective gas flow passage tubes. However, in the above explained conventional device the combustible gas passage and the auxiliary gas passage are formed within a single common plate, therefore, when the channels and the leading holes in the plate are erroneously processed and/or the threaded holes receiving the screws for securing the respective gas flow controlling elements are erroneously positioned, such device may cause a problem that the auxiliary gas possibly mixes into the combustible gas flow passages and/or oppositely the combustible gas possibly mixes into the auxiliary gas flow passage.

SUMMARY OF THE INVENTION

An object of the present invention is to provide an analysis device using chemical combustion flame having an excellent safety in which possible danger caused by such as the gas leakage and the gas mixing between the combustible gas passage and the auxiliary gas passage is further reduced.

An analysis device using chemical combustion flame according to the present invention in which chemical combustion flame is formed by making use of combustible gas and auxiliary gas, a sample is introduced into the thus formed chemical combustion flame and the photo emission and/or the photo absorption caused by the sample are measured, characterized in that the analysis device is provided with a combustible gas use plate or block having a gas flow passage for the combustible gas and an auxiliary gas use plate or block having a gas flow passage for the auxiliary gas which is independent and separated from the combustible gas use plate or block and the combustible gas use plate or block being provided with controlling elements for controlling the combustible gas flow passing through the combustible gas flow passage and the auxiliary gas use plate or block being provided with controlling elements for controlling the auxiliary gas flow passing through the auxiliary gas flow passage.

DETAILED DESCRIPTION OF THE PREFERRED EMBODIMENT

Figure 1:
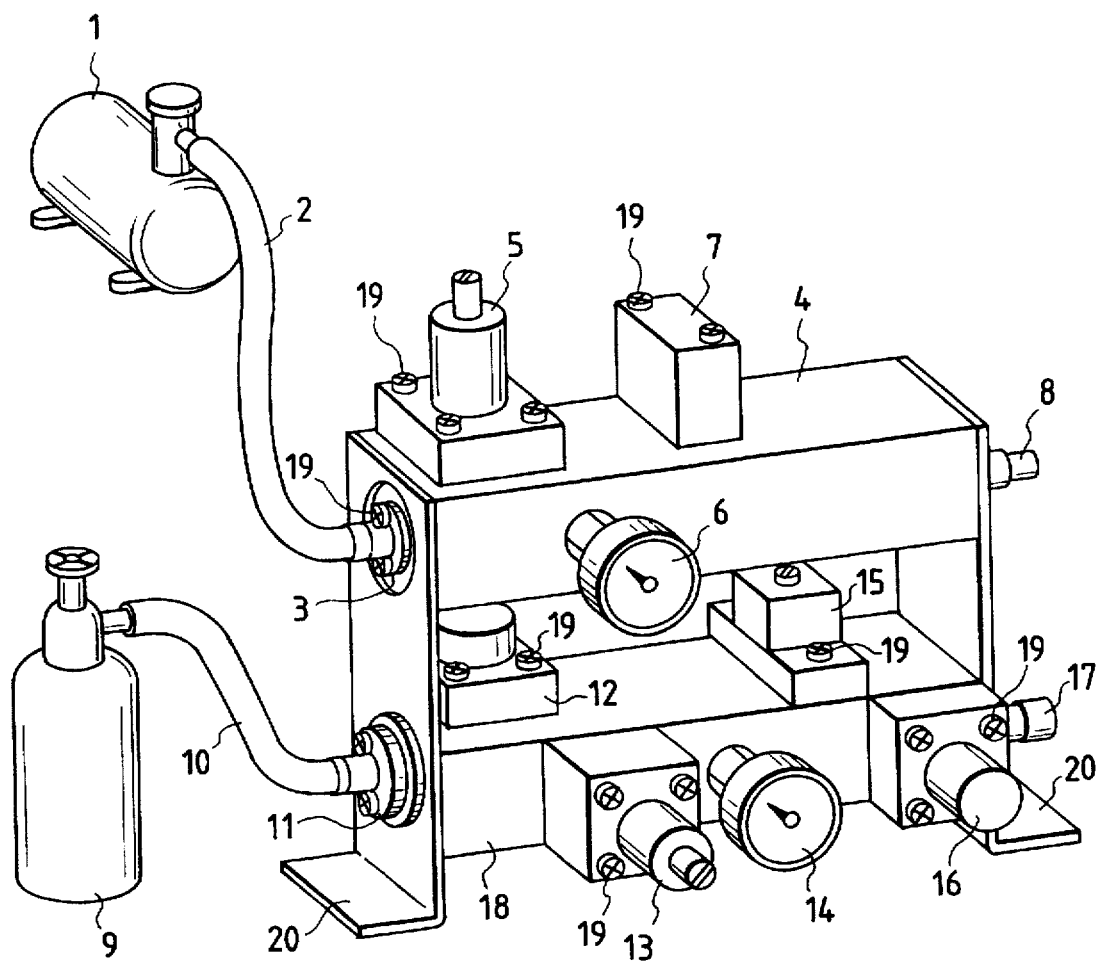
FIG. 1 is a perspective view of a major portion of an analysis device using chemical combustion flame representing one embodiment according to the present invention.
Figure 2:
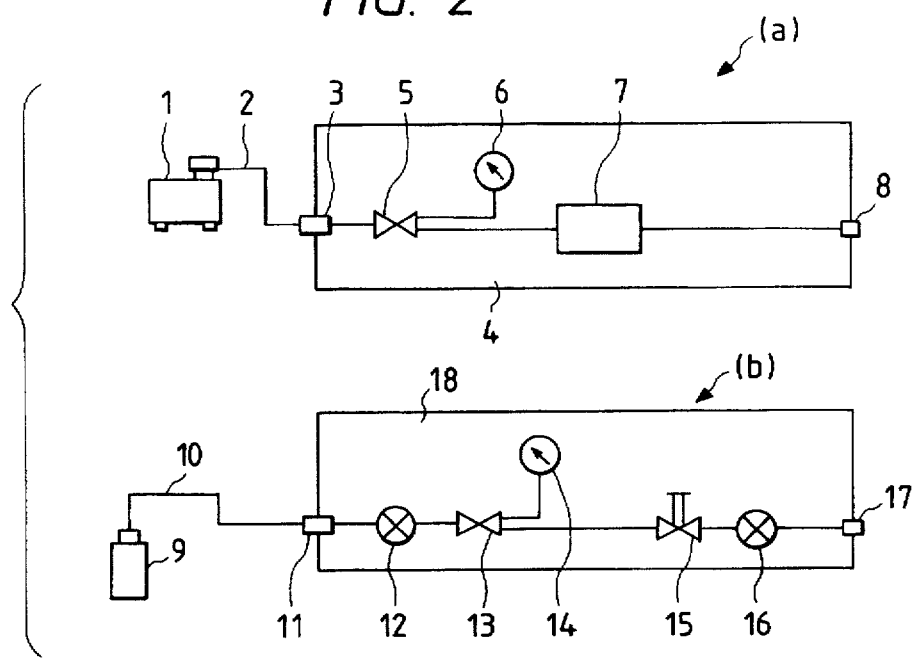
FIG. 2 is a gas flow passage diagram of the analysis device shown in FIG. 1, wherein (a) is a gas flow passage diagram for an auxiliary gas and (b) is a gas flow passage diagram for a combustible gas.

In the analysis device according to the present embodiment as shown in FIGS. 1 and 2, an auxiliary gas such as air supplied from a compressor 1 is introduced from an auxiliary gas inlet 3 via a pipe 2 to a burner (not shown) through a pressure regulator 5, a pressure meter 6, a pressure switch 7 and a connecting joint 8 and via a tube.

On the other hand, a combustible gas such as acetylene gas and propane gas supplied from a gas bomb 9 is introduced from a combustible gas inlet 11 via a pipe 10 to the burner through an electromagnetic valve 12, a pressure regulator 13, a pressure meter 14, a needle valve 15, another electromagnetic valve 16 and a connecting joint 17 further via a tube.

The auxiliary gas flow controlling elements such as the pressure regulator 5, pressure meter 6 and pressure switch 7 are secured to an auxiliary gas use block 4 made of aluminum at one of the top and bottom, right and left and front and back faces thereof by the screws 19, connect channels and leading holes formed in the auxiliary gas use block 4 to constitute a flow passage and control such as the flow rate and pressure of the auxiliary gas. Likely, the flow rate and pressure of the combustible gas supplied from the gas bomb 9 are controlled by the combustible gas flow controlling elements such as the electromagnetic valve 12, pressure regulator 13, pressure meter 14, needle valve 15, electromagnetic valve 16 which are secured on a combustible gas use block 18 made of aluminum by the screws 19.

The auxiliary gas use block 4 and the combustible gas use block 18 are coupled via a pair of coupling members 20.

Now, the operation of the present embodiment is explained. The auxiliary gas such as air supplied from the compressor 1 is introduced via the auxiliary gas inlet 3 to the pressure regulator 5 wherein the initial gas pressure of about 400 kPa is pressure-regulated to about 160 kPa and the pressure regulated gas is led to the connecting joint 8 via the pressure meter 6 and the pressure switch 7 and further introduced into the burner via the tube (both not shown).

On the other hand, the combustible gas such as acetylene gas and propane gas supplied from the gas bomb 9 is led to the combustible gas inlet 11 via the pipe 10 and then flows into the pressure regulator 13 via the electromagnetic valve 12, wherein the initial combustible gas pressure of about 180 kPa is pressure regulated to about 90 kPa and further the flow rate thereof is controlled via the needle valve 15, and then introduced to the burner (not shown) via the electromagnetic valve 16 and the connecting joint 17 and further via the tube (not shown). The air and the combustible gas introduced into the burner are mixed inside the burner and are flown out from the upper portion thereof and fired to form chemical combustion flame, which is idential with the conventional analysis device as explained in connection with FIGS. 3 through 5, therefore the illustration thereof is omitted for the sake of simplicity.

Figure 3:
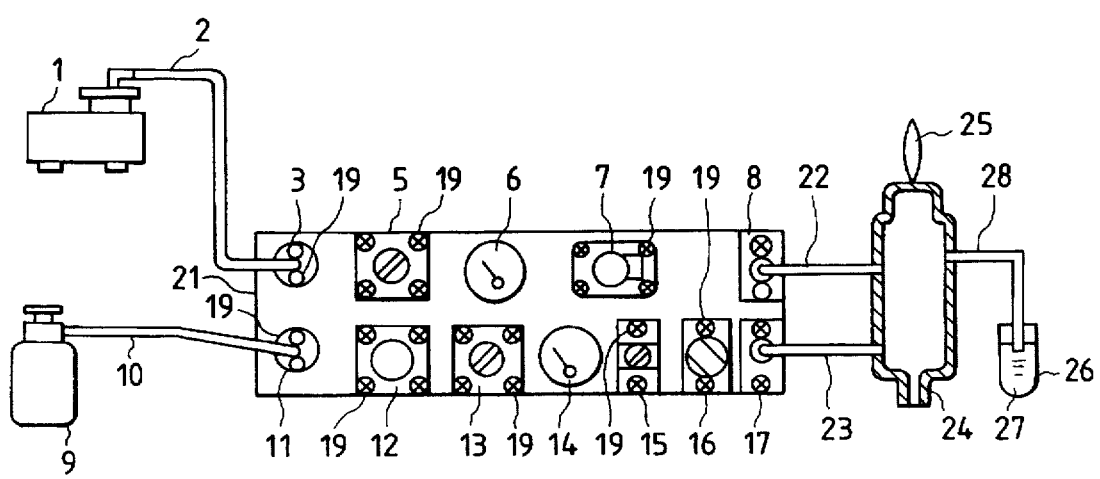
FIG. 3 is a schematic diagram of a conventional analysis device using chemical combustible flame.
Figure 4:
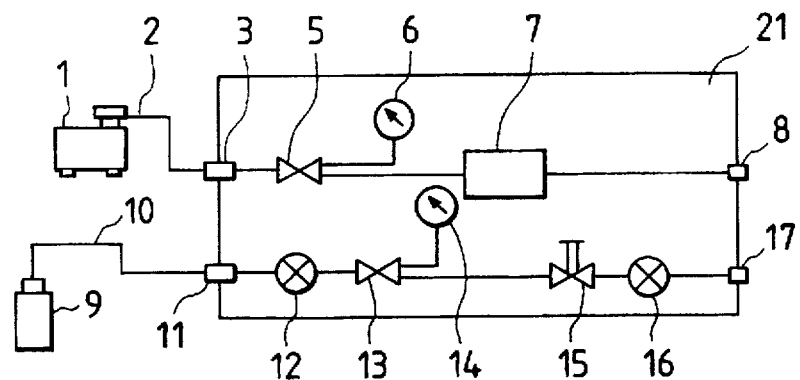
FIG. 4 is a gas flow passage diagram of the analysis device as shown in FIG. 3.
Figure 5:
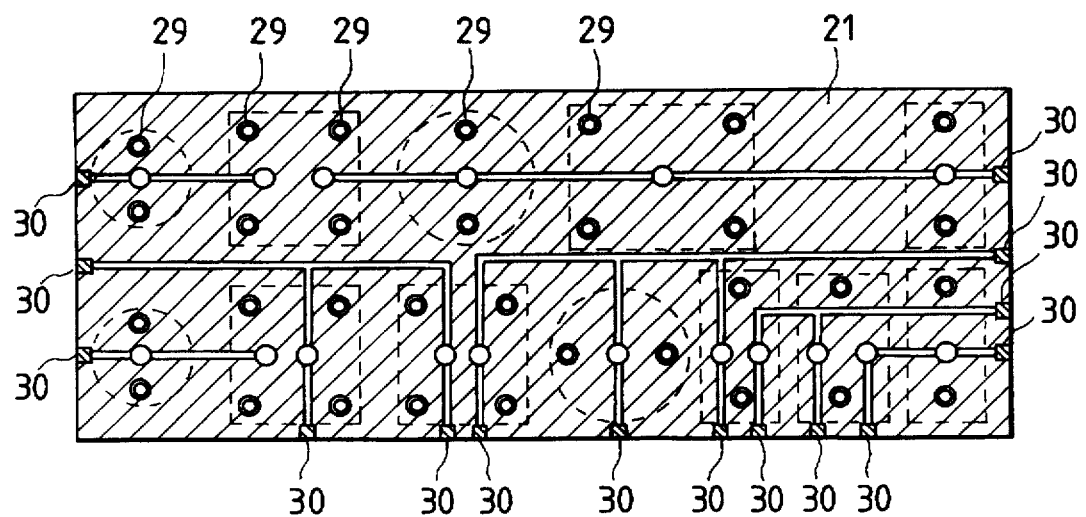
FIG. 5 is a cross sectional view of a plate constituting a gas flow controlling unit of the analysis device as shown in FIG. 3.

In the thus formed chemical combustion flame of which illustration also omitted a sample is introduced via a capillary tube like in the analysis device as explained in connection with FIGS. 3 through 5. Thereby, the sample is atomic-vaporized and the photo emission and/or photo absorption caused by the atomically vaporized sample are measured.

In the present embodiment, when the pressure of the compressor 1 drops because of possible reasons such as malfunctioning thereof and damage of the connecting portion of the connecting pipe 2, the pressure switch 7 is operated, the electromagnetic valve 12 is closed via activation of an associated electric system (not shown) and the combustible gas passage is interrupted so that back firing of the flame and disordering in analysis data due to variation of the flame are prevented.

Further, when both electromagnetic valves 12 and 16 are closed under the condition that the combustible gas such as acetylene gas is confined in the combustible gas flow passage formed inside the combustible gas use block 18, the presence or absence of the gas leakage can be confirmed by detecting whether or not the indicator of the pressure meter 14 moves.

In typical analysis devices using combustible gas such as an atomic absorption photometer using such as acetylene gas and hydrogen gas and a flame photometer using propane gas, the safety is the first rank importance because there is danger of explosion if gas leakage is by any chance caused.

Further, other than gas leakage to the outside, a gas mixing between different gas flow passages is also dangerous same as the gas leakage to the outside so that a measure for preventing such gas mixing is likely necessitated. Still further, if gas leaks to the outside and/or the gas mixes between the different gas flow passages, the flow rate of the gas and air varies and the reproducibility of the analysis result by such analysis device is directly affected and lowered.

As will be clear from the above explaination, in the analysis device making use of combustible gas which inherently possesses danger of explosion it is the uppermost importance to prevent gas leakage from the gas controlling unit to the outside as well as to prevent gas mixing between the different gas flow passages in the gas controlling unit.

As explained previously the combustible gas flow passage and the auxiliary gas flow passage are conventionally formed in a single common plate and no economical measures to acertain whether the channels and leading holes which in combination constitute the respective gas flow passages are correctly formed were available, therefore, the problem endangering the safety such as the gas mixing between the different gas flow passages was remained unsolved.

In the present embodiment, the conventional plate for securing the gas flow controlling elements is divided and separated into two, in that the auxiliary gas use block 4 and the combustible gas use block 18, therefore, such possibility is prevented that the auxiliary gas mixes into the combustible gas flow passage and oppositely the combustible gas mixes into the auxiliary gas flow passage.

Further, by means of the division and separation of the combustible gas passage and the auxiliary gas passage the respective gas flow control elements such as the auxiliary gas inlet port 3 and the connecting joint 8 can be secured any of the six faces of the respective blocks 4 and 18 as illustrated in FIG. 1 which contributes to reduce the entire size of the respective gas flow controlling units.

Further advantage of dividing and separating the combustible gas passage from the auxiliary gas passage is that when combustible gas such as propane gas of which specific gravity is heavier than that of air is used, the combustible gas flow passage unit is placed below the auxiliary gas flow passage unit in view of possible combustible gas leakage to the outside as illustrated in FIG. 1, and, oppositely, when the combustible gas such as acetylene gas of which specific gravity is lighter than that of air is used, the location of the combustible gas flow passage unit and the auxiliary gas flow passage unit is inverted or the separating distance of the both units is increased.

Further advantage of locating the both units in vertical direction is to reduced the installation area of the entire gas flow controlling unit.

According to the present invention an analysis device using chemical combustion flame having an excellent safety is provided in which possible danger caused by such as the gas leakage and the gas mixing between the combustible gas passage and the auxiliary gas passage is further reduced.

What is claimed is:

1. An analysis device using chemical combustion flame in which chemical combustion flame is formed by making use of combustible gas and auxiliary gas, a sample is introduced into the thus formed chemical combustion flame and the photo emission and/or the photo absorption caused by the sample are measured, wherein the analysis device is provided with a combustible gas use plate having a gas flow passage for the combustible gas and an auxiliary gas use plate having a gas flow passage for the auxiliary gas which is independent and separated from said combustible gas use plate, and said combustible gas use plate being provided with controlling elements for controlling the combustible gas flow passing through said combustible gas flow passage in said combustible gas used plate and said auxiliary gas use plate being provided with controlling elements for controlling the auxiliary gas flow passing through said auxiliary gas flow passage in said auxiliary gas use plate.

2. An analysis device using chemical combustion flame according to claim 1, wherein said combustible gas use plate and said auxiliary gas use plate are positioned spaced apart in vertical direction.

3. An analysis device using chemical combustion flame according to claim 2, wherein either of said combustible gas use plate or said auxiliary gas use plate which flows lighter gas than that of the other is positioned upward of the other.

4. An analysis device using chemical combustion flame according to claim 2, wherein said combustible gas use plate and said auxiliary gas use plate are spaced apart by a distance which permits installation of at least one of the controlling elements either for controlling the combustible gas flow or for controlling the auxiliary gas flow.

5. An analysis device using chemical combustion flame according to claim 3, wherein said combustible gas use plate and said auxiliary gas use plate are spaced apart by a distance which permits installation of at least one of the controlling elements either for controlling the combustible gas flow or for controlling the auxiliary gas flow.

6. An analysis device using chemical combustion flame comprising:

a combustible gas source for supplying combustible gas;

an auxiliary gas source for supplying auxiliary gas;

a burner for forming chemical combustion flame by making use of the combustible gas and the auxiliary gas introduced therein from said combustible gas source and said auxiliary gas source respectively;

a sample source from which a sample to be analyzed is fed to said burner;

a combustible gas flow controlling unit disposed between said combustible gas source and said burner and controlling the gas flow of the combustible gas from said combustible gas source to the burner; and an auxiliary gas flow controlling unit disposed between said auxiliary gas source and said burner and controlling the gas flow of the auxiliary gas from said auxiliary gas source to the burner, wherein said combustible gas flow controlling unit includes a first block member in which a plurality of combustible gas channels and a plurality of combustible gas leading holes extending from one of the faces of said first block member and reaching to at least one of said plurality of combustible gas channels and a plurality of combustible gas controlling elements secured on one of the faces of said first block member and connected to at least one of said plurality of combustible gas leading holes so as to constitute a combustible gas flow passage within said first block member, and said auxiliary gas flow controlling unit includes a second block member which is independent from and separated from said first block member and in which a plurality of auxiliary gas channels and a plurality of auxiliary gas leading holes extending from one of the faces of said second block member and reaching to at least one of said plurality of auxiliary gas channels and a plurality of auxiliary gas controlling elements secured on one of the faces of said second block member and connected to at least one of said plurality of auxiliary gas leading holes so as to constitute an auxiliary gas flow passage within said second block member.

7. An analysis device using chemical combustion flame according to claim 6, wherein said first block member carrying thereon said combustible gas controlling elements and said second block member carrying thereon said auxiliary gas controlling elements are positioned in vertical direction with a predetermined space and are connected each other by a pair of connecting plates.

8. An analysis device using chemical combustion flame according to claim 7, wherein the predetermined space between said first and second block members is determined in such a manner to permit at least one of either said combustible gas controlling elements or said auxiliary gas controlling elements to be secured one of the opposing faces of said first and second block members.

9. An analysis device using chemical combustion flame according to claim 8, wherein said first block member is positioned upward with respect to said second block member when the specific gravity of the combustible gas is lighter than that of the auxiliary gas, and said first block member is positioned downward with respect to said second block member when the specific gravity of the combustible gas is heavier than that of the auxiliary gas.

10. An analysis device using chemical combustion flame according to claim 6, wherein said combustible gas controlling elements includes a pair of electromagnetic valve disposed along said combustible gas flow passage.

11. An analysis device using chemical combustion flame according to claim 6, wherein said first and second block members are made of aluminum.

* * * * *

UNITED STATES PATENT AND TRADEMARK OFFICE
CERTIFICATE OF CORRECTION

PATENT NO. : 5,801,827
DATED : September 1, 1998
INVENTOR(S) : Kazuo MORIYA, et al.

It is certified that error appears in the above-identified patent and that said Letters Patent is hereby corrected as shown below: On the title page, Item [57], ABSTRACT, line 3, change "pressur" to --pressure--.

Column 4, line 15, change "the first" to --of first--.

Column 4, line 28, change "the uppermost" to --of uppermost--.

Column 4, line 40, delete "was".

Column 4, line 46, after "prevented" insert --in--.

Column 5, line 2, change "reduced" to --reduce--.

Column 6, line 34, after "connected" insert --to--.

Column 6, line 41, after "secured" insert --to--.

Column 6, line 54, change "valve" to --valves--.

Signed and Sealed this

Twenty-second Day of June, 1999

Attest:

Attesting Officer

Q. TODD DICKINSON

Acting Commissioner of Patents and Trademarks